United States Patent
Zimmerling et al.

(10) Patent No.: US 8,758,394 B2
(45) Date of Patent: Jun. 24, 2014

(54) IMPLANT MAGNET INSERTION AND REMOVAL TOOLS

(75) Inventors: Martin Zimmerling, Patsch (AT); Bernhard Jamnig, Innsbruck (AT); Edith Sebesta, Seefeld (AT); Franz Berger, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1272 days.

(21) Appl. No.: 12/248,114

(22) Filed: Oct. 9, 2008

(65) Prior Publication Data

US 2009/0099403 A1 Apr. 16, 2009

Related U.S. Application Data

(60) Provisional application No. 60/979,431, filed on Oct. 12, 2007.

(51) Int. Cl.
*A61B 17/50* (2006.01)
*A61M 37/00* (2006.01)

(52) U.S. Cl.
USPC ............................... 606/210; 606/211; 600/12

(58) Field of Classification Search
None
See application file for complete search history.

(56) References Cited

U.S. PATENT DOCUMENTS

| | | | | |
|---|---|---|---|---|
| 4,437,362 A | * | 3/1984 | Hurst | 294/65.5 |
| 5,002,561 A | * | 3/1991 | Fisher | 606/210 |
| 5,897,507 A | * | 4/1999 | Kortenbach et al. | 600/562 |
| 6,308,101 B1 | | 10/2001 | Faltys et al. | 607/57 |
| 2002/0188316 A1 | * | 12/2002 | Dingler | 606/205 |
| 2003/0171787 A1 | | 9/2003 | Money et al. | 607/57 |
| 2003/0181945 A1 | * | 9/2003 | Opolski et al. | 606/206 |
| 2004/0243177 A1 | | 12/2004 | Svehla et al. | 606/210 |
| 2005/0004629 A1 | | 1/2005 | Gibson et al. | 607/60 |
| 2008/0221641 A1 | | 9/2008 | Hochmair et al. | 607/57 |

FOREIGN PATENT DOCUMENTS

WO   WO 03/092326 A1   11/2003   ............. H04R 25/00

OTHER PUBLICATIONS

European Patent Office, International Search Report filed Jan. 27, 2009, PCT/US2008/079270.

* cited by examiner

*Primary Examiner* — Daniel Sullivan
*Assistant Examiner* — Melissa Javier
(74) *Attorney, Agent, or Firm* — Sunstein Kann Murphy & Timbers LLP

(57) ABSTRACT

A magnet positioning tool is described for use with an implantable device. The device has a pair of opposing positioning surfaces, at least one of which has a magnet cradle for mechanically engaging an implant magnet associated with a magnet position in the implantable device. The tool also includes a position engagement surface for engaging the implantable device when the magnet cradle is adjacent to the magnet position.

17 Claims, 5 Drawing Sheets

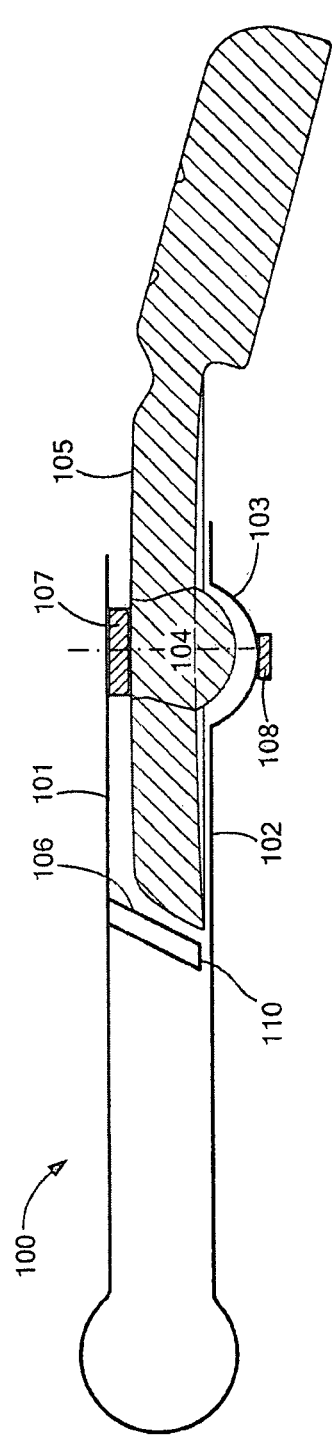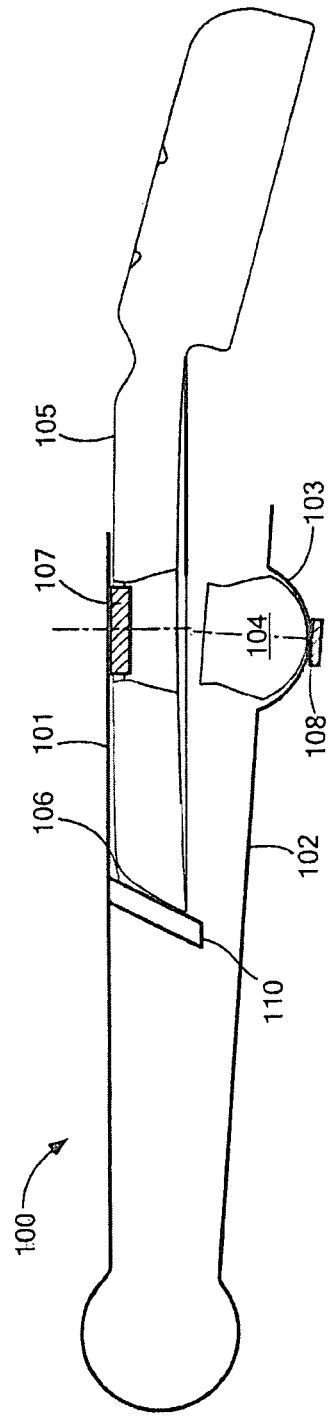

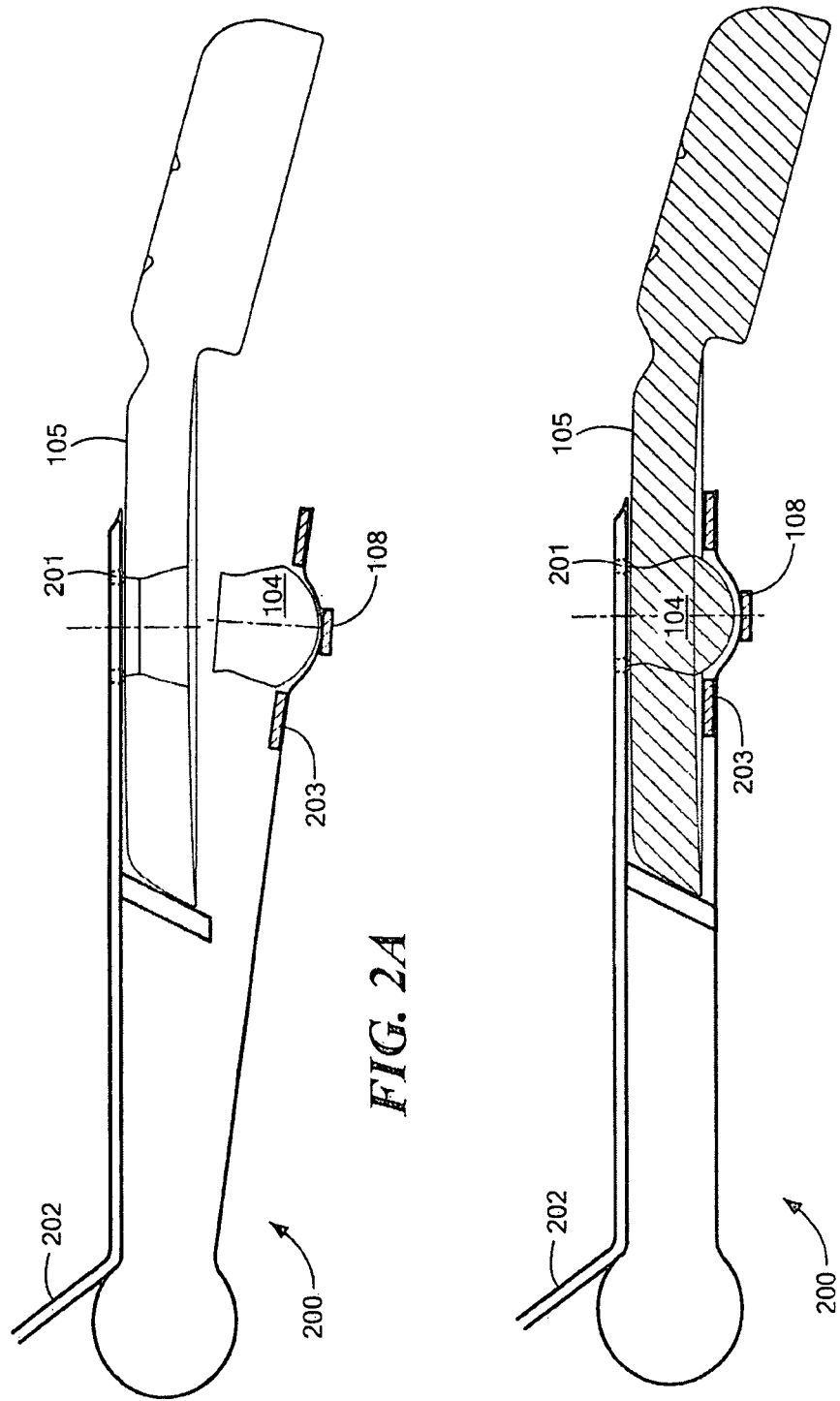

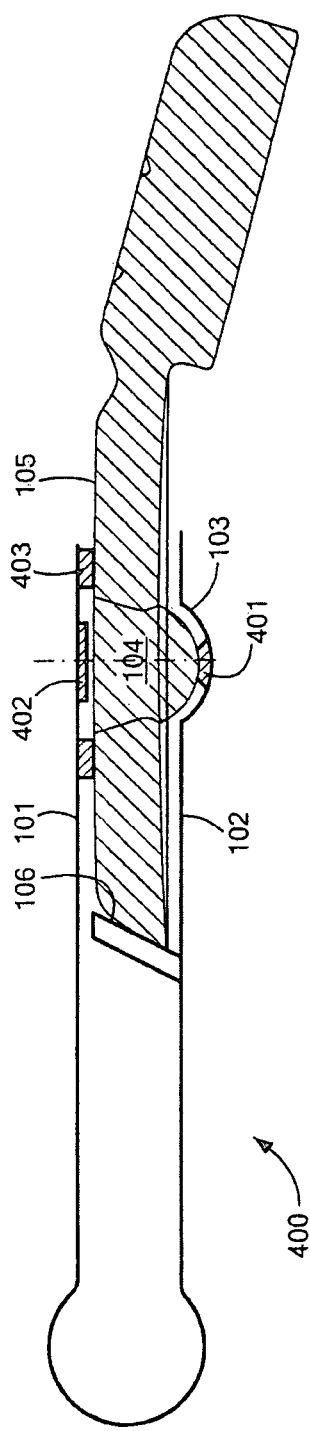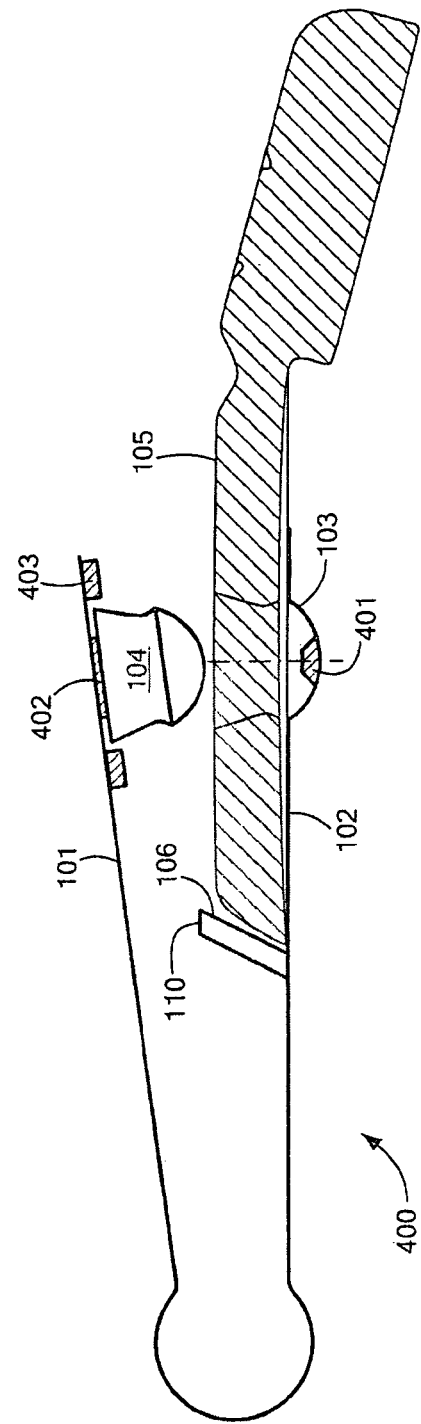

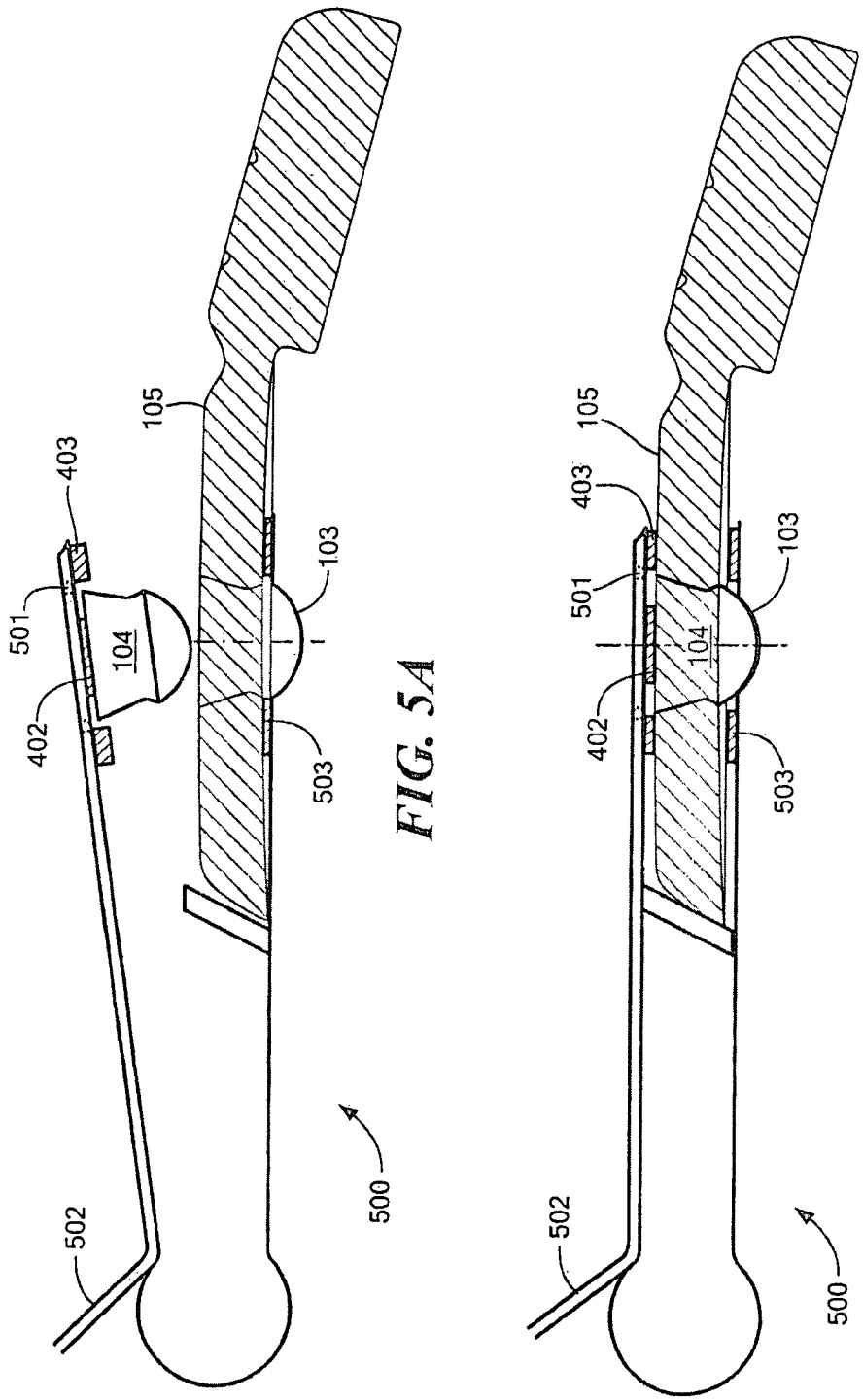

IMPLANT MAGNET INSERTION AND REMOVAL TOOLS

This application claims priority from U.S. Provisional Patent Application 60/979,431, filed Oct. 12, 2007, which is incorporated herein by reference.

FIELD OF THE INVENTION

The present invention relates to implantable medical devices, and specifically to tools and techniques for inserting and removing magnets associated with such devices.

BACKGROUND ART

Some implantable medical devices, such as cochlear implant systems, may include subcutaneous magnets which are used to hold in place various external elements such as transmission coils. But such magnets are not compatible with various medical imaging systems, for example, high field magnetic resonance imaging (MRI). To perform an MRI on a patient with an implanted magnet, pre-imaging surgery may be required first to remove the magnet, then the actual imaging may be performed, after which another post-imaging surgery is needed to replace the magnet. Besides the inconvenience of this, the actual removal and replacement of the magnet is not trivial. The magnet may be a small slippery sphere which the surgeon may have some difficulty grasping and handling. In one known design, a removable magnet is located in a silicone pocket which has an opening (a lip) at the lateral side of an implant coil, and magnet removal and replacement is accomplished by means of conventional tweezers.

SUMMARY OF THE INVENTION

Embodiments of the present invention are directed to a magnet positioning tool for use with an implantable device which includes an implant magnet. The magnet positioning tool includes a pair of opposing positioning surfaces, at least one of which has a magnet cradle for mechanically engaging an implant magnet having an associated magnet position in the implantable device. The magnet cradle may specifically include a concave spherical section for mechanically engaging a corresponding convex spherical section portion of the implant magnet. The tool also includes a position engagement surface for engaging the implantable device when the magnet cradle is adjacent to the magnet position. The magnet cradle may mechanically engage the implant magnet from either above or beneath the implantable device.

In some embodiments, the magnet cradle engages the implant magnet both mechanically and magnetically. A further specific embodiment may also include a magnet ejector projection on a positioning surface opposite to the magnet cradle for displacing the implant magnet from the magnet cradle into the magnet position when the positioning tool is engaged with the implanted device. In addition or alternatively, a flushing ring may provide flushing fluid to cleanse the magnet position in the implantable device immediately before inserting the magnet. The tool may also include a flushing channel for providing the flushing fluid to the flushing ring. A specific embodiment may also include a stopper mechanism that prevents the opposing surfaces from approaching each other beyond some insertion distance so that when the magnet is inserted by the tool, the magnet is not displaced past the magnet position in the implantable device. Some tools may further include a protective layer covering at least a portion of the tool to protect the magnet from being damaged by the tool.

BRIEF DESCRIPTION OF THE DRAWINGS

FIG. 1A-B shows cross-sectional views of a magnet removal tool according to one specific embodiment of the present invention.

FIG. 2A-B shows cross-sectional views of another magnet insertion tool according to an embodiment of the present invention.

FIG. 4A-B shows cross-sectional views of another magnet insertion tool according to an embodiment of the present invention.

FIG. 5A-B shows cross-sectional views of another magnet insertion tool according to an embodiment of the present invention.

DETAILED DESCRIPTION OF SPECIFIC EMBODIMENTS

Figure 3:
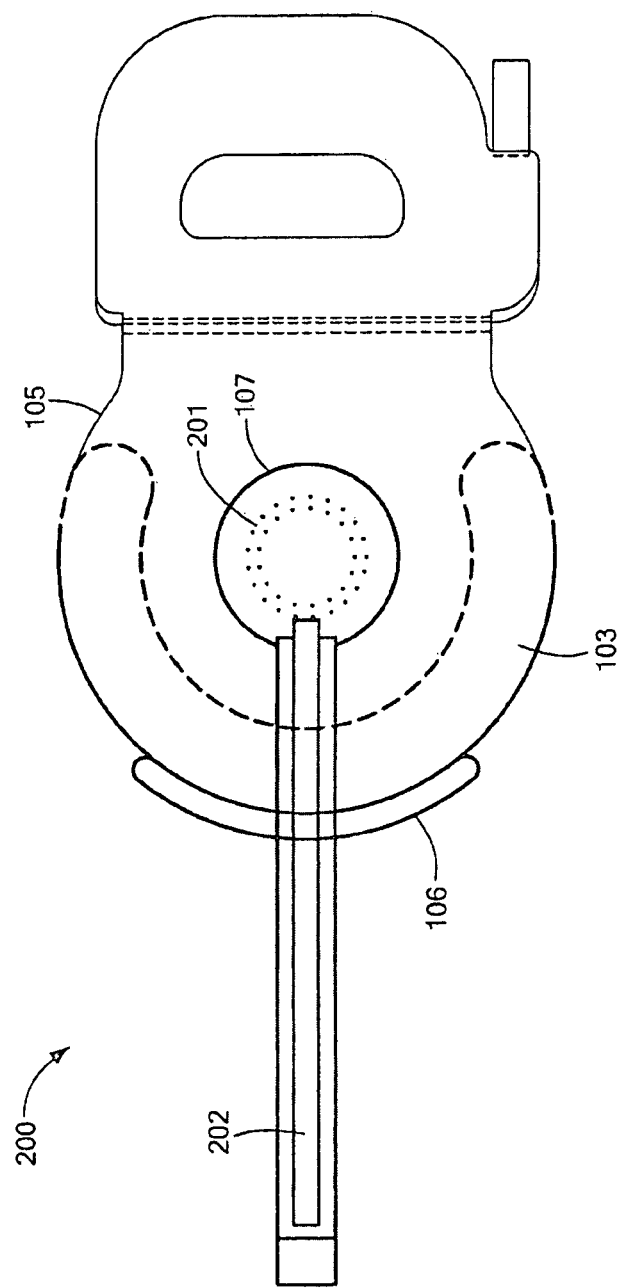
FIG. 3 show a top view of a magnet positioning tool according to an embodiment as shown in FIG. 2.

Embodiments of the present invention are directed to a magnet positioning tool for use with an implantable device. The magnet positioning tool holds the implant magnet when inserting it into or removing it from the implanted device. Such a tool limits the mechanical stress placed on the implanted device and allows the size of the incision to be kept relatively small. Appropriate design helps maintain the electrical properties (e.g. inductivity, resistance) and the mechanical integrity of various elements of the implanted device such as the coil assembly (e.g., an optimal fit between the coil assembly and the magnet or magnet housing). This also helps preserve the integrity of the hermetically sealed housings (e.g. magnet housing) in the implanted device. The tool also enables the use of faster surgical techniques.

FIG. 1A-B shows cross-section views of an embodiment of a magnet positioning tool 100 having a pair of opposing positioning surfaces 101 and 102, and a magnet cradle 103 having a concave spherical section for mechanically engaging a corresponding convex spherical section portion of an implant magnet 104. FIG. 1A shows the magnet positioning tool 100 in place around an implantable device 105 when it is ready to remove the implant magnet 104, and FIG. 1B shows the magnet positioning tool 100 after it has removed the implant magnet 104 from beneath the implantable device 105. The positioning tool 100 has a slim efficient profile (thinner than a surgeon's finger) which enables the surgical incision used for magnet removal and reinsertion to be as small as possible.

In some specific embodiments, all or part of the magnet cradle 103 may also be magnetic so that it can engage the implant magnet 104 both mechanically and magnetically. For that purpose, the magnet positioning tool 100 in FIG. 1A-B includes a magnetic button 108 on the bottom of the magnet cradle 103 for magnetically engaging the implant magnet 104. The magnetic positioning tool 100 also includes a magnet ejector projection 107 on the positioning surface 101 opposite to the magnet cradle 103 for displacing the implant magnet 104 from the implantable device 105 into the magnet cradle 103.

The magnetic positioning tool 100 includes a position engagement surface 106 for aligning the positioning tool 100 with the implantable device 105 when the magnet cradle 103 is in correct operating position adjacent to the position of the implant magnet 104 in the implantable device 105 (e.g., concentrically over an implant coil even when the implant (coil) and magnet are hidden underneath a skin flap). The magnetic positioning tool 100 also has a stopper mechanism 110 that prevents the opposing surfaces 101 and 102 from approaching each other beyond some insertion distance so that when the implant magnet 104 is inserted by the magnet positioning tool 100, the implant magnet 104 is not displaced past the magnet position in the implantable device 105.

FIG. 2A-B shows cross-sectional views and FIG. 3 shows a top view of another magnetic positioning tool 200. FIG. 2A shows the magnet positioning tool 200 when it is ready to insert a replacement magnet 104 from beneath the implantable device 105, and FIG. 2B shows the magnet positioning tool 200 after it has inserted the replacement implant magnet 104 into the implantable device 105. The magnetic positioning tool 200 includes a flushing ring 201 that provides flushing fluid to cleanse the magnet position in the implantable device 105 (e.g., the contact surface between the coil part and the magnet housing), immediately before inserting the implant magnet 104. The magnet positioning tool 200 may also include a flushing channel 202 for providing the flushing fluid to the flushing ring 201. The magnetic positioning tool 200 also has a protective layer 203 (e.g., such as Teflon®) covering some of the magnet positioning tool 200 to protect the magnet 104 from being damaged by the tool.

FIG. 4A-B shows cross-sectional views of another magnetic positioning tool 400 which engages the implant magnet 104 from above the implantable device 105. FIG. 4A shows the magnet positioning tool 400 when it is ready to remove an implant magnet 104 from above the implantable device 105, and FIG. 4B shows the magnet positioning tool 400 after it has removed the implant magnet 104. In FIG. 4 A-B, the magnet cradle 103 includes a magnet ejector projection 401 for displacing the implant magnet 104 from the implantable device 105 into a magnetic button 402 on the opposite side of the magnet positioning tool 400 that magnetically and mechanically engages the implant magnet 104. The magnet positioning tool 400 also has a protective ring 403 for protecting the surface of the implantable device 105 from the magnet positioning tool 400.

FIG. 5 A-B shows cross-sectional views of another embodiment of a magnetic positioning tool 500 which engages the implant magnet 104 from above the implantable device 105 and which includes a flushing ring 501 that provides flushing fluid to cleanse the magnet position in the implantable device 105, e.g., the contact surface between the coil part and the magnet housing, immediately before inserting the magnet 104. The magnet positioning tool 500 also includes a flushing channel 502 for providing the flushing fluid to the flushing ring 501. Lower protective ring 503 and upper protective ring 403 protect the surface of the implantable device 105 from the magnet positioning tool 500.

Although various exemplary embodiments of the invention have been disclosed, it should be apparent to those skilled in the art that various changes and modifications can be made which will achieve some of the advantages of the invention without departing from the true scope of the invention.

What is claimed is:

1. A magnet positioning tool for use with an implantable device, the tool comprising:
    a pair of opposing positioning surfaces, at least one of the positioning surfaces having a magnet cradle for mechanically engaging an implant magnet in the implantable device, the magnet cradle configured to magnetically engage the implant magnet; and
    a stopper mechanism having a position engagement surface, the stopper mechanism projecting from one of the opposing positioning surfaces toward the other opposing positioning surface and configured to prevent the opposing surfaces from approaching each other beyond an insertion distance, the position engagement surface configured to laterally engage the implantable device and to align the implantable device relative to the magnet cradle.

2. A magnet positioning tool according to claim 1, further comprising:
    a magnet ejector projection on a positioning surface opposite to the magnet cradle, the magnet ejector projection protruding from the positioning surface and configured to displace the implant magnet from the implantable device into the magnet cradle when the position engagement surface is engaged with the implantable device.

3. A magnet positioning tool according to claim 1, further comprising:
    a flushing ring on a positioning surface opposite to the magnet cradle for providing flushing fluid to cleanse a magnet position in the implantable device before inserting the implant magnet.

4. A magnet positioning tool according to claim 3, further comprising:
    a flushing channel for providing the flushing fluid to the flushing ring.

5. A magnet positioning tool according to claim 1, wherein the magnet cradle includes a concave spherical section for mechanically engaging a corresponding convex spherical section portion of the implant magnet.

6. A magnet positioning tool according to claim 1, further comprising:
    a protective layer covering at least a portion of the tool to protect the implant magnet from being damaged by the tool.

7. A magnet positioning tool according to claim 1, wherein the magnet cradle mechanically engages the implant magnet from beneath the implantable device.

8. A magnet positioning tool according to claim 1, wherein the magnet cradle mechanically engages the implant magnet from above the implantable device.

9. A magnet positioning tool for use with an implantable device, the tool comprising:
    a pair of opposing positioning surfaces, at least one of the positioning surfaces having a magnet cradle for mechanically engaging an implant magnet in the implantable device, the positioning surface opposite to the magnet cradle having a magnetic button configured to magnetically engage the implant magnet; and
    a stopper mechanism having a position engagement surface, the stopper mechanism projecting from one of the opposing positioning surfaces toward the other opposing positioning surface and configured to prevent the opposing surfaces from approaching each other beyond an insertion distance, the position engagement surface configured to laterally engage the implantable device and to align the implantable device relative to the magnet cradle.

10. A magnet positioning tool according to claim 9, wherein the magnet cradle further includes a magnet ejector projection that protrudes from its bottom surface and is configured to displace the implant magnet from the implantable device to the magnetic button when the position engagement surface is engaged with the implantable device.

11. A magnet positioning tool according to claim 9, further comprising:

a flushing ring on a positioning surface opposite to the magnet cradle for providing flushing fluid to cleanse a magnet position in the implantable device before inserting the implant magnet.

12. A magnet positioning tool according to claim 11 further comprising:
a flushing channel for providing the flushing fluid to the flushing ring.

13. A magnet positioning tool according to claim 9, wherein the magnet cradle includes a concave spherical section for mechanically engaging a corresponding convex spherical section portion of the implant magnet.

14. A magnet positioning tool according to claim 9, further comprising:
a protective layer covering at least a portion of the tool to protect the implant magnet from being damaged by the tool.

15. A magnet positioning tool according to claim 9, wherein the magnet cradle mechanically engages the implant magnet from beneath the implantable device.

16. A magnet positioning tool according to claim 9, wherein the magnet cradle mechanically engages the implant magnet from above the implantable device.

17. A magnet positioning tool according to claim 1, wherein the magnet cradle includes a magnetic button on its bottom surface configured to magnetically engage the implant magnet.

* * * * *